United States Patent [19]

Pronovost

[11] Patent Number: 5,075,220

[45] Date of Patent: Dec. 24, 1991

[54] DETERMINATION OF A CHLAMYDIAL OR GONOCOCCAL ANTIGEN USING A POSITIVELY-CHARGED IONICALLY BINDING SUPPORT

[75] Inventor: Allan D. Pronovost, San Diego, Calif.

[73] Assignee: Eastman Kodak Company, Rochester, N.Y.

[21] Appl. No.: 255,923

[22] Filed: Oct. 7, 1988

[51] Int. Cl.$^5$ .................... C12Q 1/00; C12Q 1/28; G01N 33/53

[52] U.S. Cl. .................... 435/7.36; 435/28; 436/518; 436/531; 436/540

[58] Field of Search .............. 436/510, 511, 518, 531, 436/590, 808, 823; 435/7, 28, 810, 805, 7.36

[56] References Cited

U.S. PATENT DOCUMENTS

| | | | |
|---|---|---|---|
| 4,241,045 | 12/1980 | Gaafar . | |
| 4,340,479 | 7/1982 | Pall . | |
| 4,492,900 | 2/1985 | Abram et al. | 436/511 |
| 4,497,899 | 2/1985 | Armstrong et al. | 436/510 |
| 4,828,983 | 5/1989 | McClune | 435/14 |
| 4,830,960 | 5/1989 | Appleton | 436/518 |
| 4,874,691 | 10/1989 | Chandler | 435/7 |
| 4,959,303 | 9/1990 | Milburn et al. | 435/7.36 |

FOREIGN PATENT DOCUMENTS

| | | |
|---|---|---|
| 0173500 | 5/1986 | European Pat. Off. . |
| 0264036 | 2/1988 | European Pat. Off. . |
| 274911 | 7/1988 | European Pat. Off. . |
| 84/03055 | 8/1984 | World Int. Prop. O. . |

OTHER PUBLICATIONS

ECldik et al., Conditions for Reproducible Detection of Calmodulin and Sloob in Immunoblots, Biochem & Biophys. Res. Comm., vol. 124, No. 3, 1984, pp. 752–759.

Backman et al., Gonococcal Serovar Diestribution in Stockholm . . ., Acta. Pathol Microbiol. Immunol Scand. Sect B. Microbiol 93(3):225–232, 1985.

Pall Corp. trade literature PSD-750a, Mar. 1983, pp. 1–20.

Pall Corp. trade literature NM-900c, Sep. 1984, pp. 1–28.

Pall Corp. trade literature: "Product information", pp. 1–3, Dec. 1986.

*Primary Examiner*—Sam Rosen
*Attorney, Agent, or Firm*—J. Lanny Tucker

[57] ABSTRACT

Antigens extracted from chlamydial or gonococcal organism are rapidly and ionically bound directly to a polymeric solid support which has cationic groups on its surface. The support is substantially free of any antibody or other biological compound reactive with the antigen. Ionically bound antigen is then contacted with suitable chlamydial or gonococcal antibodies to form a bound immunological complex which is detected in suitable fashion, for example by using a labeled antibody. The entire assay, carried out at room temperature, requires less than 30 minutes and is highly sensitive.

19 Claims, No Drawings

DETERMINATION OF A CHLAMYDIAL OR GONOCOCCAL ANTIGEN USING A POSITIVELY-CHARGED IONICALLY BINDING SUPPORT

FIELD OF THE INVENTION

The present invention relates to a procedure for the detection of chlamydial or gonococcal organisms in a biological specimen. More particularly, it relates to the detection of an antigen extracted from any of these organisms using a positively-charged solid support.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is Chlamydia trachomatis (herein C. trachomatis) which is one of two microbial species of the genus Chlamydiaceae, order Chlamydiales. There are 15 or more strains of this species which are the causes of a number of human ocular and genital diseases including trachoma, inclusion conjunctivitis, lymphogranuloma venereum, nongonococcal urethritis and proctitis. Infection from C. trachomatis is pervasive in the general population so that it is believed that there are millions of cases each year of nongonococcal urethritis alone.

Gonorrhea is a disease usually transmitted by sexual contact caused by a bacterium of the Neisseria genus, especially N. gonorrhoeae. The disease has plagued mankind for thousands of years, and although antibiotics have helped control its spread, it still persists in epidemic proportions in many parts of the world. The importance of detection and treatment of this organism is well recognized. N. meningitidis and N. lactamica are also species of considerable medical and diagnostic interest.

Because of the widespread nature of these diseases, there is considerable interest in having a rapid, simple and reliable test for detection of chlamydial and gonococcal organisms. Considerable research has been carried out to find useful ways to extract detectable antigen from chlamydial organisms. See for example, U.S. Pat. Nos. 4,427,782 (issued Jan. 24, 1984 to Caldwell et al) and 4,663,291 (issued May 5, 1987 to Rose) and E.P. Publications 174,106 (Becton) and 193,431 (Caldwell et al).

Assays for C. trachomatis and N. gonorrhoeae carried out using a solid support are described in U.S. Pat. Nos. 4,497,899 and 4,497,900, respectively (both issued Feb. 5, 1985 to Armstrong et al and Abram et al, respectively). The described assays are performed by extracting antigen from the organism and coating it on a bare solid support. The coated antigen is then detected with either one or two antibodies, one of which is suitably labeled. The critical feature of the assays appears to be the use of a solid support for attachment which is untreated or uncoated with any material. That is, there is no chemical or immunological binding between the support and antigen. Attachment of antigen is apparently achieved by incubating the coated support for an extended time sufficient to cause adsorption of antigen thereon (Col. 2, lines 51-55 of U.S. Pat. No. 4,497,899). From the examples of this patent, this time is determined to be at least 30 minutes at elevated temperature (37° C.). The entire assay described in U.S. Pat. No. 4,497,899 takes at least 3 hours to perform. A similar but somewhat quicker assay is described in U.S. Pat. No. 4,497,900 for N. gonorrhoeae (see Cols. 4 and 5).

It would be desirable to have a much more rapid test for chlamydial or gonococcal organisms which has high reliability and can be performed at room temperature.

SUMMARY OF THE INVENTION

The problems noted above are overcome with a method for the determination of a chlamydial or gonococcal antigen comprising:

A. contacting chlamydial or gonococcal antigen extracted from a specimen suspected of containing chlamydial or gonococcal organisms, respectively, with a polymeric solid support which is substantially free of any biological compound reactive with said antigen, and which has a multiplicity of positively charged groups on the surface thereof so as to ionically bind the chlamydial or gonococcal antigen directly to the solid support, B. within about 10 minutes of the contact, separating unbound materials from the ionically bound antigen and contacting the bound chlamydial or gonococcal antigen with chlamydial or gonococcal antibody, respectively, so as to form an immunological complex on the support, and C. within about 10 minutes of the antibody-antigen contact, separating the immunological complex from uncomplexed antibody and determining the presence of the complex on the support as a measure of the amount of chlamydial or gonococcal antigen, respectively, in the specimen.

The assay of this invention is rapid, reliable and simple to use. For example, it can be carried out in less than 30 minutes at room temperature. It is highly reliable for detecting extracted chlamydial antigen (such as from C. trachomatis), and particularly the lipopolysaccharide antigen. It can also be used to rapidly and sensitively detect gonococcal antigens (such as from N. gonorrhoeae).

These advantages are achieved in the present invention from the use of a positively-charged polymeric solid support to which the antigen is bound for detection. The binding of antigen to the support is by ionic means. Binding of the antigen is preferential to other proteins or cell components which generally fail to attach to the ionically charged support.

The use of ionic attachment of the antigen is considerably faster than mere antigen adsorption taught in U.S. Pat. Nos. 4,497,899 and 4,497,900 (noted above). Particularly, the present invention is generally carried out, after extraction, within about 30 minutes. In many assays, even the extraction step can not be carried out within the 30 minutes period. Moreover, the lengthy adsorption process of the art requires incubation at several points at elevated temperatures (37° C.) which necessitates elaborate analytical equipment. The present invention can be carried out at room temperature with minimal equipment and technical skills required.

DETAILED DESCRIPTION OF THE INVENTION

The present invention is a method for determining the presence of *C. trachomatis* (or other chlamydial species), or the presence of *N. gonorrhoeae* (or other gonococcal species) in a biological specimen which has been obtained from a patient using any suitable medical or diagnostic techniques. Such specimens include, for example, swab specimens obtained from the cervix, urethra, throat or anus of a patient, and body fluids such as synovial fluid or fluid from lesions. The biological specimens so obtained are suspected of containing chlamydial bacterial organisms which comprise the chlamydial or gonococcal antigen (or mixture thereof) to be determined.

While the assay can be carried out to detect antigens from intact chlamydial or gonococcal organisms, it is usually desirable to extract the antigens from the organisms in order to increase assay sensitivity. Standard techniques can be used for lysing the organism to release antigen including, for example, solvent dilution or high pH lysing solutions, enzyme treatment and physical agitation such as sonication or centrifugation. Heating is described as a lysing technique in E.P. Publication 183,383 (published June 4, 1986). The use of anionic detergents or salts such as sodium dodecyl sulfate and deoxycholate is described in U.S. Pat. Nos. 4,497,899, 4,497,900 (both noted above) and 4,663,291 (issued May 5, 1987 to Rose).

In a preferred embodiment, the present invention can be used to detect the chlamydial lipopolysaccharide (glycolipid group) antigen (as described, for example, in E.P. Publication 193,431, published Sept. 3, 1986). Extraction procedures are also described therein. In another embodiment, the detected antigen can be the chlamydial major outer membrane protein of the organism which comprises about 60% of the total associated outer membrane protein. This antigen and methods of extraction are described in U.S. Pat. No. 4,427,782 (issued Jan. 24, 1984 to Caldwell et al). In some instances, a mixture of these chlamydial antigens will be detected using the present invention. In still other embodiments, the invention is used to detect one or more gonococcal antigens (IA or IB protein), or mixtures of antigens from individual gonococcal strains.

A preferred extraction composition is described in detail in copending U.S. Ser. No. 255,928 filed on even date herewith by Pronovost, Mauck, Sullivan, Greer and Gilbert and entitled "High pH Extraction Composition and Its Use to Determine a Chlamydial, Gonococcal or Herpes Antigen". The central feature of that composition is the presence of an alcoholamine and its high pH. Further details of this preferred composition are provided below in relation to the examples.

In addition, it may be desirable to use a protease in the extraction procedure to break down whole blood and mucous. This is described in copending U.S. Ser. No. 255,922 filed on even date herewith by Gilbert, Mauck and Stowers and entitled "Use of a Protease in the Extraction of Chlamydial, Gonococcal and Herpes Antigens".

Once antigen is extracted from the organism, it is desirable, although not essential, that the specimen be prefiltered to remove cell debris, particulate matter and other unwanted materials prior to further handling. Prefiltering can be carried out in a suitable container having a filter of some type.

Extraction can be carried out in any suitable container, including devices specially designed for extraction of antigen. Useful devices are known in the art, including U.S. Pat. No. 4,746,614 (issued May 24, 1988 to Devaney, Jr. et al).

Extracted antigen is contacted with a polymeric solid support which has a multiplicity of positively charged groups on the surface thereof. These positively charged groups produce a positive surface charge on the support, that is, a positive zeta potential over a wide pH range. Zeta potential is known as the potential between the support and a fluid in contact with it, and is generally determined by measuring the voltage developed as the fluid is contacted with a support. It can also be measured by fragmenting a charged support and dispersing it in the fluid followed by measurement of the potential of the resulting suspension. Such measurements can be made using standard physicalchemical techniques. Any positively charged chemical radical which produces the desired zeta potential on the support is useful in the practice of this invention.

For example, the support can be constructed of any natural or synthetic polymeric material with suitable cationic groups thereon which will ionically bind to the extracted antigen. Useful polymers include polyesters, polyamides, polyethyleneimines, polycarbonates, cellulosic materials, addition polymers prepared from ethylenically unsaturated vinyl monomers and others known in the art having the requisite charged groups. Generally, the cationic groups are quaternary ammonium salts, quaternary phosphonium salts, quaternary sulfonium salts, quaternary pyridinium salts, quaternary pyrimidinium salts or quaternary imidazolium salts. Quaternary ammonium salts are preferred.

The support can be composed of a polymer which can have such cationic groups as part of the polymeric structure. These groups can be incorporated therein by preparing the polymer from starting materials (such as monomers) which contain cationic groups. Alternatively, the polymers can be derivatized or modified by reacting them with a reagent to form the positively charged groups, for example by reacting a polymer containing a chloromethylphenyl group with a trialkylamine to form a quaternary ammonium salt on the polymer backbone. Alternatively, a polymer containing an imidazole group can be reacted with chloroethanol to form a quaternary imidazolium salt. The groups can be also incorporated by forming the polymers from positively-charged starting materials (for example, positively-charged ethylenically unsaturated polymerizable monomers).

Alternatively, the support can comprise a nonionic polymer which is coated with another material (generally another polymer) which is appropriately charged. For example, a polyamide, polyester, or an addition polymer can be coated with a second polymer which has a multiplicity of cationic groups.

A preferred polymeric solid support is a microporous membrane manufactured and sold by Pall Corp. as Posidyne ® or Biodyne ®-B membranes. These supports comprise a nylon membrane coated with a polyester which has quaternary ammonium groups in the pores. Other positively-charged membranes would also be useful in the practice of this invention.

The polymeric support can be configured in any suitable form, such as beads, films, membranes, gels or pellets. A membrane is preferred as described in above.

The support described herein can be used in combination with other equipment (bottles, test tubes, swabs, beakers or cups) in order carry out the assay. Alternatively and preferably, the support is a microporous membrane which is fitted into a disposable test device in which the assay can be carried out and all fluids accommodated. Useful configurations of test devices are known in the art including U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May, 1984 to Liotta). Particularly useful devices are described and claimed in copending and commonly assigned U.S. Ser. Nos. 19,810 (filed Feb. 27, 1987 by Hinckley) and 98,248 (filed Sept. 18, 1987 by Hinckley).

Almost immediately upon contact of the antigen with the charged support, the antigen is bound by ionic means directly to the support. By "directly" is meant that the antigen is not bound through a linking moiety, or biological compound (such as an antibody) which is attached to the support. While some adsorption of antigen to the support may occur, it is believed to be insignificant because the assay is carried out in insufficient time and under conditions not suitable for a substantial amount of the antigen to adsorb to the support. In other words, too little antigen is adsorbed in the present invention within the time frame of the assay to provide sensitive detection of chlamydial or gonococcal antigen. It is also apparent that the antigen is preferentially bound to the support as opposed to other proteins, cell components or debris which may be present in the test specimen or reagents used in the assay.

Within about 10 minutes, and preferably within 1 to 5 minutes, of the contact, the bound antigen is contacted with chlamydial or gonococcal antibody so as to form an immunological complex on the support. Fluid and unbound materials can be removed quickly at the same time. If the assay is carried out using a disposable test device, the support can be a microporous membrane through which fluid and unbound materials in the specimen are allowed to flow through as the antigen is bound to the membrane.

The antibody used in this assay is specifically immunoreactive with one or more chlamydial or gonococcal strains (depending upon what organism is of interest). It can be polyclonal or monoclonal. If polyclonal, it is commercially available or prepared in various animals using known techniques employing an antigen common to the strain of organism to be detected. A single antibody or mixture thereof can be used. For example, antibody to either the chlamydial lipopolysaccharide or major outer membrane protein antigen, or antibodies to both antigens can be used in the assay. Preferably, the antibodies are monoclonal which are either commercially available or prepared using standard hybridoma technology. Useful procedures for preparing antibodies are described, for example, in E.P. Publication 193,431 and U.S. Pat. No. 4,427,782 (noted above).

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent compounds, chemiluminescent compounds, phosphorescent compounds, biotin or its derivatives, avidin or its derivative, ferritin, magnetizable particles, dyed particles, gold sols, dye sols, colored *Staphylococcus aureus* cells and other readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates and dye-providing reagents are also needed.

In a particularly preferred embodiment, the label is peroxidase, and at some point in the assay, hydrogen peroxide and suitable dye-forming reagents are added to provide a detectable dye. For example, useful dye-providing reagents include leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a preferred embodiment, the chlamydial or gonococcal antibody is not labeled, and detection of the antibody-antigen complex formed and bound to the support is accomplished using a second antibody (described below) which is specific to the unlabeled antibody and is appropriately labeled.

The chlamydial or gonococcal antibody can be contacted with the bound antigen in the presence of one or more proteins which reduce nonspecific interactions on the support. Useful proteins are well known and include, for example, casein, α-casein, fetal bovine serum and procine gamma globulin. A particularly useful blocking composition comprises a protein and an amphoteric surfactant, as described and claimed in copending U.S. Ser. No. 255,925 filed on even date herewith by Pronovost and entitled "Immunological Reagent Composition and Its Use in the Determination of Chlamydial or Gonococcal Antigens."

Once the bound antigen has been contacted with the chlamydial or gonococcal antibody, an ionically bound immunological complex is formed on the support. To hasten the formation of this complex, the antibody and antigen are generally incubated at a temperature of from about 15° to about 30° C. for up to 10 minutes. Preferably, the incubation is carried out at from about 18° to about 25° C. (that is, room temperature) for from 1 to 5 minutes. These mild incubation conditions are in sharp contrast to the 30 minutes at 37° C. described as necessary for adsorption of chlamydial antigen to bare uncharged supports in U.S. Pat. No. 4,497,899 (noted above).

After the incubation and within about 10 minutes of the antibody-antigen contact, the bound complex is washed one or more times with a wash solution which generally has a pH of from about 7 to about 12. The solution preferably contains one or more surfactants to aid in separating unbound materials from the bound complex. Particularly useful surfactants are cationic surfactants, as described in copending U.S. Ser. No. 255,924, filed on even date herewith by Pronovost and Gilbert and entitled "Wash Composition Containing a Cationic Surfactant and Its Use in Chlamydial and Gonococcal Determinations."

In the embodiment described above where the chlamydial or gonococcal antibody is labeled, the assay procedure after washing is to detect the label directly or indirectly after addition of the appropriate reagents. This is done relatively quickly after washing the bound complex, that is generally within about 10 minutes, and preferably within about 1 to about 5 minutes. If desired, label detection can be hastened with incubation if the reagents warrant it. The label is then detected using standard equipment and procedures.

In the preferred embodiment, the chlamydial or gonococcal antibody is unlabeled, and after washing the bound complex, it is contacted with an antibody directed to the unlabeled antibody. This second antibody (that is, an anti-antibody) is appropriately labeled with any of the labels described above. The antibody can be monoclonal or polyclonal and either purchased or prepared using known techniques. In a chlamydial assay, the anti-antibody is preferably a polyclonal antibody which is reactive with either of the lipopolysaccharide or major outer membrane protein antibodies.

After this contact, the resulting antigen-antibody-antibody complex which is ionically bound to the support is incubated for up to about 10 minutes at a temperature of from about 15° to about 30° C., and preferably for about 1 to about 5 minutes at from 18° to 25° C.

Further washing is carried out to remove uncomplexed materials, and suitable enzyme substrates or other needed reagents are added to provide a detectable species. The bound antigen-antibody-labeled antibody complex is then detected on the support using standard radiometric, colorimetric, fluorescent or other detection techniques.

The following examples are provided to illustrate, but not limit the scope of, the present invention.

To perform these examples, the mouse monoclonal antibody to the chlamydial lipopolysaccharide antigen was prepared using standard hybridoma technology and mouse cell line and stored in a solution of phosphate buffered saline (pH 7.4) containing 0.01% (by weight) sodium azide. The antibody composition used in the assay was prepared by adding a sample (19 μl) of the antibody solution to a phosphate buffered saline solution (diluting 1:800) containing casein (0.5 weight %) as a blocking protein and Lonzaine® C amphoteric surfactant (0.01 weight %, available from Lonza, Inc.), then filtered through a 0.22 μmeter filter to obtain a working solution.

The labeled polyclonal antibody used was a goat anti-mouse IgG antibody conjugated to horseradish peroxidase (obtained from BioRad Laboratories). This conjugate was diluted to about 1:2000 in a phosphate buffered saline solution containing 0.5% (by weight) casein and 0.01% (by weight) Lonzaine® C amphoteric surfactant, and filtered through a 0.22 μmeter filter to obtain a working solution.

An antigen extraction solution was prepared from the following components: sodium azide (0.027 molar), sodium chloride (0.27 molar), ethanolamine hydrochloride (0.47 molar), disodium ethylenediaminetetraacetic acid (0.045 molar), Emcol® CC-36 cationic surfactant (quaternary ammonium chlorides of polypropoxy-t-amines, available from Witco Chemical, 0.45 weight percent from a 10% solution in methanol) and sodium hydroxide (0.66 molar, pH 11).

EXAMPLE 1

Determination of Chlamydia trachomatis Lipopolysaccharide Antigen Using Two Antibodies This example demonstrates the practice of the present invention using two antibodies, one directed against the lipopolysaccharide *C. trachomatis* antigen, and the second being labeled and directed to the chlamydial antibody.

The assay was carried out in a disposable test device designed similar to that described in copending and commonly assigned U.S. Ser. No. 19,810 (noted above). It contained a microporous membrane having quaternary ammonium groups on the surface (commercially available as the Pall Biodyne®-B membrane, Pall Corp.). Prior to use, the membrane was treated with Zonyl TM FSN (a nonionic fluorinated surfactant available from DuPont).

Elementary body protein *C. trachomatis* organisms was obtained from Professor W. J. Newhall (Indiana University). The lipopolysaccharide antigen was extracted at about 20° C. by turning the specimen on a swab in an extraction device containing the extraction composition described above for about 5 minutes. Citrate (100 μl of a 0.7 molar solution) was then added to lower the pH to about 7-8, followed by addition of a protease [P8038 from Sigma Chemical Co., 7-14 units/mg, 2 mg/ml of a solution containing 0.877 g NaCl and 0.242 g tris(hydroxymethyl)aminomethane hydrochloride in 100 ml water, pH 8.0]. Extraction was continued for another 5 minutes at about 20° C., after which hydrogen peroxide and sodium hydroxide (pH above 10) were added to remove endogenous catalase, peroxidase and myeloperoxidase.

The treated speciment was then filtered through a 5 micrometer membrane to remove unwanted matter. The filtered extract (120 μl) was added to a test well of the disposable test device. Specimen fluid was allowed to flow through the membrane upon contact. Within a few seconds, all fluid had drained through the membrane and the monoclonal antibody solution (120 μl) described above was added to the test well and allowed to drain.

The immunological complex bound to the membrane was washed twice with a solution (160 μl) of Emcol® CC-9 cationic surfactant (0.75 weight %) in phosphate buffered saline solution (pH 7.2).

Immediately after the second wash, the peroxidase-labeled polyclonal antibody (120 μl) was added to the test well, and the fluid allowed to drain through immediately. Incubation at about 20° C. was carried out again for about 5 minutes to form an antigen-antibody-labeled antibody complex ionically bound to the membrane.

After washing twice with the wash solution (160 μl) described above, a dye-providing composition (120 μl) was added to the test well. This composition included hydrogen peroxide (10 mmolar), 2-(4-hydroxy-3-methoxyphenyl)-4,5-bis(4-methoxyphenyl)imidazole leuco dye (0.005 weight %), poly(vinyl pyrrolidone)(1 weight %), 4'-hydroxyacetanilide (5 mmolar) and diethylene triaminepentaacetic acid (10 mmolar).

After about 5 minutes at room temperature, a red dye was observed in the test well indicating the presence of chlamydial antigen obtained from the specimen. The entire assay after extraction of antigen was performed in less than 30 minutes.

EXAMPLE 2

Determination of Chlamydia trachomatis Lipopolysaccharide Antigen Using One Antibody This example is similar to Example 1 except that only one antibody was used in the assay. This antibody was a peroxidase-labeled mouse monoclonal antibody to the lipopolysaccharide antigen of *C. trachomatis*. This labeled antibody was obtained using standard hybridoma technology.

The antigen was extracted from elementary body protein using a mixture of polyoxyethylene-9-lauryl ether (0.05% by weight, 80 μl), Zonyl TM FSN (1 weight %, 80 μl) and ethylenediaminetetraacetic acid (20 mmolar, 80 μl) in phosphate buffered saline solution. The saline solution volume varied from 560 μl for a buffered control solution (no antigen) to 510 μl for samples containing 5750 pg of antigen. Extraction was carried out for 10 minutes at 45° C., vortexed for 10 seconds and cooled to room temperature.

Posidyne ® membranes in a disposable test device were prewet with polyoxyethylene-9-lauryl ether (0.005 weight %, 100 μl), Zonyl TM FSN (0.1 weight %) and ethylenediaminetetraacetic acid (2 mmmolar), then dried at 37° C. for 15 minutes.

The extracted antigen solutions (200 μl) having varying concentrations of antigen (288, 575, 1150, 2875 and 5750 pg) and the control solution were added to individual disposable devices, and the fluids were allowed to drain through.

A solution (200 μl) of peroxidase-labeled antibody conjugate, diluted 1:450 in commercially available instant nonfat dry milk (1 weight %), fetal bovine serum (1 weight %) in 0.05 molar phosphate buffered saline solution (pH 7.2) was added and the reaction mixture was incubated in the test device for 5 minutes at room temperature with fluid kept on top of the membrane by negative pressure. The fluid was then allowed to drain through the membrane.

A wash solution (500 μl) containing Emcol ® CC-9 cationic surfactant (0.75 weight %) in phosphate buffered saline solution was added to the test devices and allowed to drain.

The leuco dye solution (50 μl) described above was added to the test devices with the fluid kept on the top of the membrane by negative pressure. After a few seconds, the fluid was allowed to drain and dye allowed to form.

After visual reading and grading of the dye density, a gradual increase in color was seen with an increase in the amount of antigen tested. No dye was observed with the control solution.

EXAMPLE 3

COMPARATIVE EXAMPLE

This example compares the present invention to the Abbott Chlamydiazyme ® assay which is similar to that described in U.S. Pat. No. 4,497,899 (noted above).

Lipopolysaccharide antigen was extracted from elementary body protein (obtained from W. J. Newhall of Indiana University) with ethanolamine (1 weight %), sodium hydroxide (0.02 normal) in tricine buffer (0.05 molar, pH 8.75) for 10 minutes at room temperature to provide solutions containing various amounts of antigen (10 to 10,000 pg).

The assay of the prior art was carried out according to directions in the package insert (insert 83-1293/R4, December, 1985). These directions were similar to that described in Example 1 of U.S. Pat. No. 4,497,899 (noted above). The total time for the assay was at least 5 hours.

The assay of this invention was carried out as follows:
Posidyne ® membranes in a disposable test device were prewet with polyoxyethylene-9-lauryl ether (0.005 weight %, 100 μl), Zonyl TM FSN (0.1 weight %) and Emcol ® CC-9 cationic surfactant (0.75 weight %).

The extracted antigen solutions (200 μl) having varying concentrations of antigen (10-10,000 pg) were added to individual disposable devices and fluid was allowed to drain simultaneously.

A solution (200 μl) of polyclonal antibody to the lipopolysaccharide antigen (described above), diluted 1:1500 in phosphate buffered saline solution containing commercially available instant nonfat dry milk (1 weight %) and fetal bovine serum (1 weight %), or casein (0.05 weight %) and Lonzaine ® C amphoteric surfactant (0.01 weight %) was added to the test devices with the fluid kept on the membranes by negative pressure. After incubation at room temperature for 5 minutes, the fluid was allowed to drain.

A wash solution (500 μl) containing Emcol ® CC-9 cationic surfactant (0.75 weight %) in phosphate buffered saline solution was added to the test devices and allowed to drain.

A solution of peroxidase-labeled anti-chlamydial antibody conjugate (200 μl), diluted 1:1000 in phosphate buffered saline solution (0.05 molar) containing commercially available instant nonfat dry milk (1 weight %), fetal bovine serum (1 weight %), or casein (0.05 weight %) and Lonzaine ® C amphoteric surfactant (0.01 weight %) was added and the reaction mixture was incubated in the test device for 5 minutes at room temperature with fluid kept on the membranes. The fluid was then allowed to drain through the membrane.

A wash solution (500 μl) containing Emcol ® CC-9 cationic surfactant (0.75 weight %) in phosphate buffered saline solution was added to the test devices and the fluid was allowed to drain through.

The leuco dye solution (50 μl) described above was added to the test devices with fluid retained in the membranes. After a few seconds, the fluid was allowed to drain and the dye to form.

After reading and grading of the dye density, a gradual increase in color was seen with an increase in the amount of antigen tested with the present invention as well as the prior art assay. The present invention required only 30–45 minutes at room temperature, whereas the prior art assay required a minimum of 5 hours with the incubation steps carried out at 37° C.

The invention has been described in detail with particular reference to preferred embodiments thereof, but it will be understood that variations and modifications can be effected within the spirit and scope of the invention.

I claim:

1. A method for the determination of a chlamydial or gonococcal antigen comprising:
   A. contacting chlamydial or gonococcal antigen extracted from a specimen suspected of containing chlamydial or gonococcal organisms, respectively, with a polymeric solid support which is substantially free of any biological compound reactive with said antigen, and which has a multiplicity of positively charged groups on the surface thereof so as to ionically bind the chlamydial or gonococcal antigen directly to the solid support, B. within about 10 minutes of the contact, separating unbound materials from the ionically bound antigen and contacting the bound chlamydial or gonococcal antigen with chlamydial or gonococcal antibody, respectively, so as to form an immunological complex on the support, and C. within about 10 minutes of the antibody-antigen contact, separating the immunological complex from uncomplexed antibody and determining the presence of the complex on the support as a measure of the amount of chlamydial or gonococcal antigen, respectively, in the specimen, steps A through C being carried out within about 30 minutes.

2. The method of claim 1 wherein said chlamydial or gonococcal antibody is enzyme-labeled, and said complex determination is accomplished using a dye-providing composition which comprises a substrate for said enzyme.

3. The method of claim 2 wherein said enzyme is peroxidase, said substrate is hydrogen peroxide and said dye-providing composition comprises a leuco dye which provides a dye in the presence of peroxidase and hydrogen peroxide.

4. The method of claim 1 wherein said chlamydial or gonococcal antibody is labeled with a radioisotope.

5. The method of claim 1 wherein said chlamydial or gonococcal antibody is unlabeled and, after step B and before step C, said antibody-antigen complex is contacted with a labeled antibody to said chlamydial or gonococcal antibody to form a labeled antibody-antibody-antigen complex.

6. The method of claim 5 wherein said label is an enzyme.

7. The method of claim 1 which is carried out using a disposable test device in which said polymeric solid support is mounted as a microporous membrane in said device.

8. A method for the determination of a chlamydial or gonococcal organisms comprising:

A. extracting chlamydial or gonococcal antigen from chlamydial or gonococcal cells, respectively, in a biological specimen, B. contacting said chlamydial or gonococcal antigen with a polymeric solid support which is substantially free of any antibody for said antigen and which has a multiplicity of positively charged groups on the surface thereof so as to ionically bind said antigen directly to said solid support, C. within about 5 minutes of said contact, separating said unbound materials from said ionically bound antigen and contacting said bound antigen with unlabeled chlamydial or gonococcal antibody, respectively, so as to form an immunological complex on said support, D. separating said complex from uncomplexed materials, E. contacting said complex with a labeled anti-antibody to said chlamydial or gonococcal antibody so as to form a labeled antibody-antibody-antigen complex, F. within about 5 minutes of said contacting step E, separating said labeled complex from uncomplexed materials, and G. determining said labeled complex on said support as a measure of the amount of chlamydial or gonococcal organism in said specimen, steps A through G being carried out within about 30 minutes.

9. The method of claim 8 wherein said polymeric solid support has a multiplicity of quaternary ammonium charges on the surface thereof.

10. The method of claim 8 wherein said antibody label is an enzyme.

11. The method of claim 10 wherein said labeled complex is determined by contacting it with a dye-providing composition comprising a substrate for said enzyme.

12. The method of claim 11 wherein said enzyme is peroxidase, said substrate is hydrogen peroxide and said dye-providing composition comprises a leuco dye which provides a dye upon the interaction of peroxidase and hydrogen peroxide.

13. The method of claim 8 for the determination of a chlamydial organism.

14. The method of claim 13 wherein the major outer membrane protein of said chlamydial organism is extracted and detected.

15. The method of claim 13 wherein the lipopolysaccharide antigen of said chlamydial organism is extracted and detected.

16. The method of claim 8 wherein said bound antigen is a gonococcal IA or IB protein which is contacted with a mixture of two or more gonococcal antibodies directed to said protein.

17. A method for the determination of the lipopolysaccharide antigen of *Chlamydia trachomatis* comprising:

A. extracting lipopolysaccharide antigen from *Chlamydia trachomatis* organisms in a biological specimen, B. contacting said extracted antigen with a polymeric solid support which is substantially free of any antibody for said antigen and which has a multiplicity of quaternary ammonium groups on the surface thereof so as to ionically bind said antigen directly to said support, C. within less than about 1 minute of said contact, separating uncomplexed materials from said ionically bound antigen and contacting said bound antigen with an unlabeled monoclonal chlamydial antibody to said antigen so as to form an immunological complex on said support, D. incubating for less than 5 minutes at room temperature, E. separating said complex from uncomplexed materials by washing, F. contacting said complex with a peroxidase-labeled antibody to said chlamydial antibody so as to form a peroxidase-labeled antibody-antibody-antigen complex, and incubating for up to about 5 minutes at room temperature, G. separating said labeled complex from uncomplexed materials by washing, H. adding a dye-providing composition comprising hydrogen peroxide and a triarylimidazole leuco dye which provides a dye in the presence of peroxidase and hydrogen peroxide, and I. determining the amount of said dye on said support as a measure of the amount of *Chlamydia trachomatis* in said specimen, steps B through I being carried out within about 30 minutes.

18. The method of claim 17 carried out using a disposable test device in which said polymeric solid support is mounted as a microporous membrane in said device.

19. The method of claim 18 wherein said biological specimen is prefiltered after extraction and prior to addition to said test device.

* * * * *